US012629122B2

(12) United States Patent　　(10) Patent No.: US 12,629,122 B2
Schulze-Ganzlin et al.　　(45) Date of Patent: May 19, 2026

(54) INTRAORAL X-ray SYSTEM WITH FUNCTIONAL SWITCH IN THE X-ray DEVICE FOR THE USE OF DIFFERENT SENSOR TYPES

(71) Applicant: DENTSPLY SIRONA Inc., York, PA (US)

(72) Inventors: Ulrich Schulze-Ganzlin, Lorsch (DE); Kai Lindenberg, Wersau (DE)

(73) Assignee: Dentsply Sirona, Inc., York, PA (US)

( * ) Notice: Subject to any disclaimer, the term of this patent is extended or adjusted under 35 U.S.C. 154(b) by 157 days.

(21) Appl. No.: 18/576,876

(22) PCT Filed: Jul. 5, 2022

(86) PCT No.: PCT/EP2022/068507
　　§ 371 (c)(1),
　　(2) Date: Jan. 5, 2024

(87) PCT Pub. No.: WO2023/280805
　　PCT Pub. Date: Jan. 12, 2023

(65) Prior Publication Data
　　US 2025/0000471 A1　Jan. 2, 2025

(30) Foreign Application Priority Data

Jul. 6, 2021　(EP) ..................................... 21183848

(51) Int. Cl.
　　*A61B 6/51*　　　(2024.01)
　　*A61B 6/00*　　　(2006.01)
(52) U.S. Cl.
　　CPC .............. *A61B 6/512* (2024.01); *A61B 6/542* (2013.01); *A61B 6/563* (2013.01)
(58) Field of Classification Search
　　CPC .......... A61B 6/512; A61B 6/542; A61B 6/563
　　See application file for complete search history.

(56) References Cited

U.S. PATENT DOCUMENTS 6,898,268 B2　5/2005　Maekilae et al.
2014/0010350 A1　1/2014　Godzinsky
(Continued)

FOREIGN PATENT DOCUMENTS

EP　　1859659　　11/2007
EP　　3673810 A1　7/2020
(Continued)

OTHER PUBLICATIONS

International Search Report; PCT/EP2022/068507; Sep. 30, 2022 (completed); Oct. 13, 2022 (mailed).
(Continued)

*Primary Examiner* — Uzma Alam
*Assistant Examiner* — Mamadou Faye
(74) *Attorney, Agent, or Firm* — SCHWEGMAN LUNDBERG & WOESSNER, P.A.

(57)　　ABSTRACT

The present invention relates to an intraoral X-ray system comprising: an intraoral X-ray device equipped with an automatic exposure control (AEC) functionality and connectable to a cloud and a computer, characterized in that at least one intraoral X-ray sensor is connectable to the intraoral X-ray device, and the intraoral X-ray device comprises a functional switch which, in an initial identification process, recognizes the sensor type of the at least one connected intraoral X-ray sensor, and activates an associated mode (M; M'; M"), wherein the intraoral X-ray system comprises one or more of the following modes (M; M'; M"): a mode (M") for intraoral X-ray sensor side detection of an exposure level, a mode (M') for intraoral X-ray device, computer or cloud side detection of an exposure level, a mode (M) without detection of an exposure level.

4 Claims, 3 Drawing Sheets

(56)        References Cited

U.S. PATENT DOCUMENTS

| | | | | |
|---|---|---|---|---|
| 2015/0342464 A1* | 12/2015 | Wundrak | ............... | A61B 5/742 |
| | | | | 433/215 |
| 2016/0262715 A1* | 9/2016 | Charnegie | .............. | A61B 6/465 |
| 2017/0188987 A1 | 7/2017 | Liu | | |
| 2019/0209117 A1* | 7/2019 | Duewer | ................. | A61B 6/545 |

FOREIGN PATENT DOCUMENTS

| | | |
|---|---|---|
| EP | 4115812 | 1/2023 |
| JP | 2024525569 | 7/2024 |
| WO | 9603917 A1 | 2/1996 |
| WO | 2023280805 | 1/2023 |

OTHER PUBLICATIONS

Written Opinion of the International Searching Authority; PCT/EP2022/068507; Sep. 30, 2022 (completed); Oct. 13, 2022 (mailed).

"International Application Serial No. PCT EP2022 068507, International Preliminary Report on Patentability mailed Jan. 18, 2024", 9 pgs.

"European Application Serial No. 21183848.7, Response Filed Jul. 4, 2025 Communication under Rule 71(3) mailed Mar. 4, 2025", 21 pgs.

"European Application Serial No. 22744684.6, Noting of loss of rights pursuant to Rule 1121 EPC mailed Feb. 27, 2024", 2 pgs.

"European Application Serial No. 21183848.7, Extended European Search Report mailed Dec. 16, 2021", w Machine English Translation, 29 pgs.

"European Application Serial No. 21183848.7, Response filed Jun. 21, 2023 to Extended European Search Report mailed Dec. 16, 2021", w English Claims, 35 pgs.

* cited by examiner

INTRAORAL X-ray SYSTEM WITH FUNCTIONAL SWITCH IN THE X-ray DEVICE FOR THE USE OF DIFFERENT SENSOR TYPES

CROSS-REFERENCE TO RELATED APPLICATIONS

This is a National Phase application of International Application No. PCT/EP2022/068507, filed Jul. 5, 2022, which claims the benefit of and priority to European Application Ser. No. 21183848.7, filed on Jul. 6, 2021, which are herein incorporated by reference for all purposes.

TECHNICAL FIELD OF THE INVENTION

The present invention relates to an intraoral X-ray system with automatic exposure control (AEC) functionality, comprising an intraoral X-ray sensor and a dental X-ray device.

BACKGROUND OF THE INVENTION

The automatic exposure control (AEC), namely the AEC technique is well known, also in the dental field for intraoral X-ray with digital X-ray image receivers, see e.g., EP1859659A1 and U.S. Pat. No. 6,898,268 B2.

X-ray image detectors have an optimized dynamic range for typical exposure situations in intraoral X-ray diagnostic. Under-exposed recordings are characterized by increased noise, while overexposed areas can no longer resolve the signal due to saturation effects of the pixels. Using the AEC technique, the saturation limit can be resolved by taking multiple exposures and summing up the individual recordings. By lowering the saturation limit, the X-ray image receiver can be optimized for low exposures. With this constellation, the user can specifically determine the minimum image quality required in each case, depending on the indication, in order to keep the patient dose as low as possible.

The exposure situation can be measured with a Scout Shot. Information on the exposure level of this first recording is used for this purpose. This indicates which maximum value of a certain number of pixels has been reached or exceeded. It can also be a relative value with reference to a maximum permissible value, e.g., in percent to the saturation limit. Information on the exposure level can also contain the respective histogram.

In AEC X-ray systems with Scout Shot, rapid evaluation of the pre-exposed images is required to determine the complete X-ray exposure in order to reduce motion artifacts that can be caused by movements of the recording geometry during the recording session. Up to now, the evaluation of the exposure level of the scout shot has been carried out detached from the intraoral X-ray sensor (hereinafter also referred to as "sensor" for short) by an evaluation unit located in the X-ray device (or in the connected computer). The procedure to date is as follows:

1. Sensor detects the $1^{st}$ shot
2. Sensor partially or completely transmits the $1^{st}$ shot to the X-ray device
3. Evaluation unit analyzes $1^{st}$ shot in the X-ray device
4. Evaluation unit determines exposure level for the $2^{nd}$ shot
5. Sensor detects the $2^{nd}$ shot
6. Sensor transmits the $2^{nd}$ shot to the X-ray device
7. Evaluation unit calculates the summed image from the $1^{st}$ shot and $2^{nd}$ shot in the X-ray device Generally, the intraoral X-ray device with AEC functionality is connected to a computer or cloud. The X-ray sensor, which is set to recording readiness, detects the X-ray image. After exposure, the X-ray image data is read out from the X-ray detector and forwarded to the computer.

SUMMARY OF THE INVENTION

One objective of the present invention is to provide an intraoral X-ray sensor with integrated AEC functionality.

Another objective of the present invention is to provide an intraoral X-ray system with a mode switch that allows the use of different types of sensors, including an intraoral X-ray sensor with or without AEC functionalities.

The intraoral X-ray system according to the invention comprises an intraoral X-ray device which is equipped with Automatic Exposure Control (AEC) functionality, and connectable to a cloud and a computer. At least one intraoral X-ray sensor is connectable to the X-ray device. Further, the X-ray device comprises a functional switch that, in an initial identification process, recognizes the sensor type of the at least one connected X-ray sensor and activates an associated mode. The intraoral X-ray system comprises one or more of the following modes: a mode for intraoral X-ray sensor side detection of an exposure level, a mode for intraoral X-ray device, computer or cloud side detection of an exposure level, a mode without detection of an exposure level.

In the following description, different X-ray sensor types and the associated modes are explained.

AEC Plus Mode and an Intraoral X-Ray Sensor With Exposure Level Detection for Use With an X-Ray System Having AEC Functionality According to the present invention, in the AEC Plus mode, the analysis of the scout image or video stream with respect to the exposure level is performed by the IO (intraoral) X-ray sensor, not by the IO X-ray device or other system components, such as a computer. For this purpose, the video stream can be used, for example, as an independent sequence of individual images.

If the above evaluation is moved to the IO X-ray sensor (hereinafter also referred to as "sensor" for short), the data transfer and the complexity on the side of the IO X-ray device are reduced. The process according to the invention is then e.g., as follows:

1. Sensor detects the $1^{st}$ shot (scout shot);
2. Evaluation unit (e.g. an exposure analysis unit of the sensor) analyzes $1^{st}$ shot and compiles information on the exposure level;
3. Information on the exposure level, as well as sensor properties if applicable, is transmitted to decision unit outside the sensor;
4. The decision unit uses this and other information to determine the exposure parameters of further shots;
5. According to this decision, none or one, or more exposures are detected by the sensor;
6. Sensor transmits individual recordings and/or (optionally) at least one summed recording to the IO X-ray unit or PC.

A key feature of the present invention is, that the electronics assigned to the IO X-ray sensor (e.g., exposure analysis unit) is capable of detecting information about the exposure level of the scout image or video stream and communicating this information to the IO X-ray device. This reduces the initialization effort and speeds up the process.

The IO X-ray device, in particular the decision unit of the IO X-ray device or other system components, uses this information of the exposure level and other specifications preferably sensor-specific properties, required image quality, indication, kV adjustment for dual energy, increased dynamic range (high dynamic range (HDR)), dose-dependent noise behavior, etc. to determine exposure parameters e.g., number of recordings, exposure time, tube current and tube voltage, for subsequent exposures. This could be one further exposure, but also several or no further exposure.

In the case of a video stream, when a value calculated by the decision unit of the X-ray device is reached, the exposure is preferably stopped by the X-ray device.

Preferably, the IO X-ray sensor head or the IO X-ray sensor connector is a possible accommodation for the evaluation unit (e.g., exposure analysis unit). Alternatively, said sensor head could be wirelessly connected to the IO X-ray device so that no connector is required.

AEC Mode and an Intraoral X-Ray Sensor Without Exposure Level Detection for Use With an X-Ray System With AEC Functionality According to the present invention, in the AEC mode, the analysis of the scout image or video stream with respect to the exposure level is performed only by the X-ray device or by other system components. The AEC Plus mode is different from the AEC mode, in which the above mentioned analysis takes place in the X-ray sensor and not in the IO X-ray device.

Standard Mode and Intraoral X-Ray Sensor Without Exposure Level Detection for Use With X-Ray System Without AEC Functionality According to the present invention, in the standard mode, no analysis of the scout image or video stream is performed with respect to the exposure level by neither the intraoral X-ray sensor nor the X-ray device/system.

BRIEF DESCRIPTION OF THE DRAWINGS

In the following description, the present invention will be explained in more detail by means of embodiments with reference to the drawings, wherein.

Figure 1:
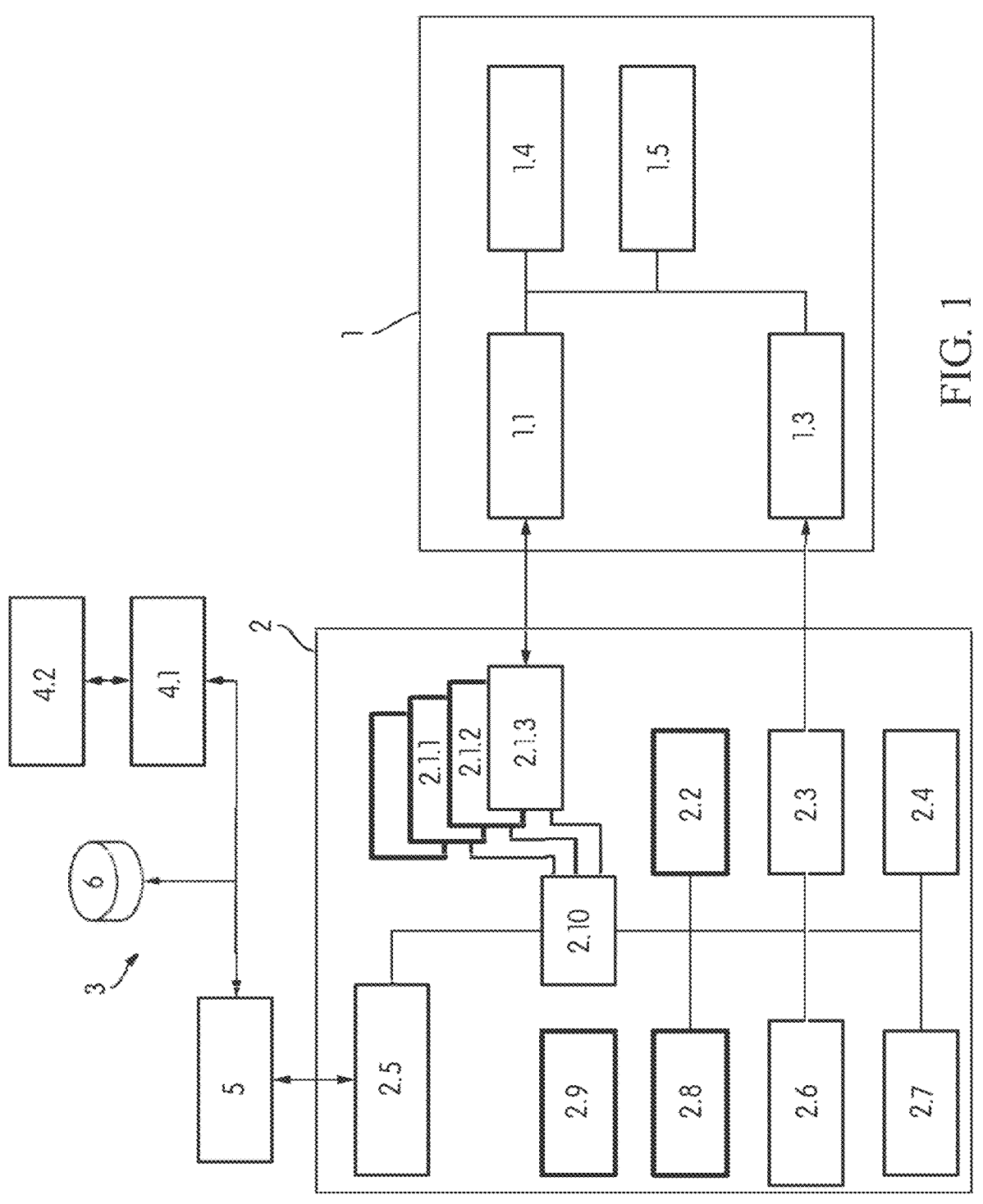
FIG. 1 is a schematic representation of an intraoral X-ray system to which a standard IO X-ray sensor for operation in a standard mode is connected.

The functional blocks with a thick border in the illustrations are not necessarily activated in the respective mode.

DETAILED DESCRIPTION OF THE INVENTION

The reference numbers shown in the drawings designate the elements listed below, which are referred to in the following description of the exemplary embodiments.

1. Intraoral X-ray sensor (sensor type for standard mode)
1' Intraoral X-ray sensor (sensor type for AEC mode)
1" Intraoral X-ray sensor (sensor type for AEC Plus mode)

Figure 2:
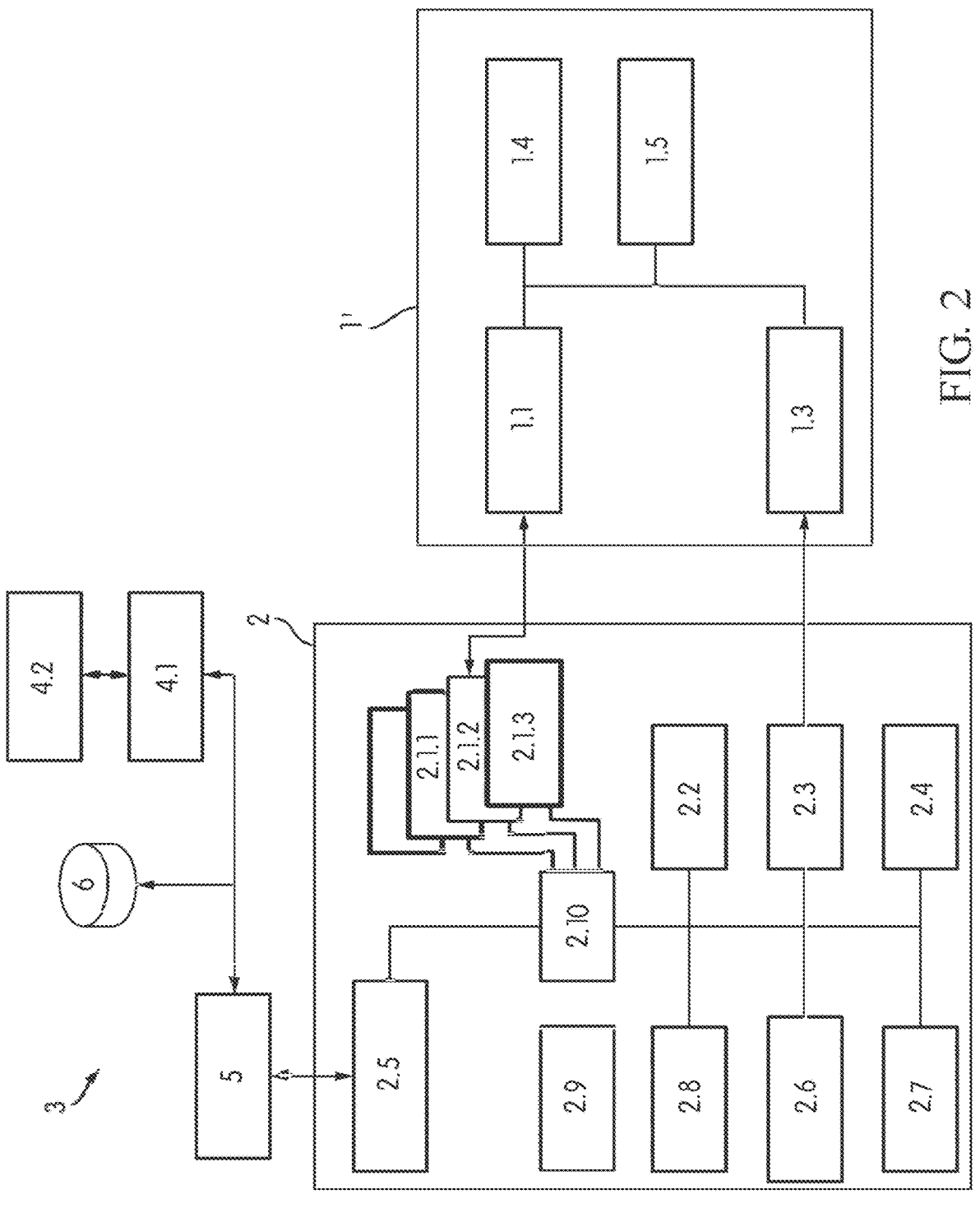
FIG. 2 is a schematic representation of an intraoral X-ray system with AEC functionality to which an IO X-ray sensor for operation in an AEC mode is connected.
Figure 3:
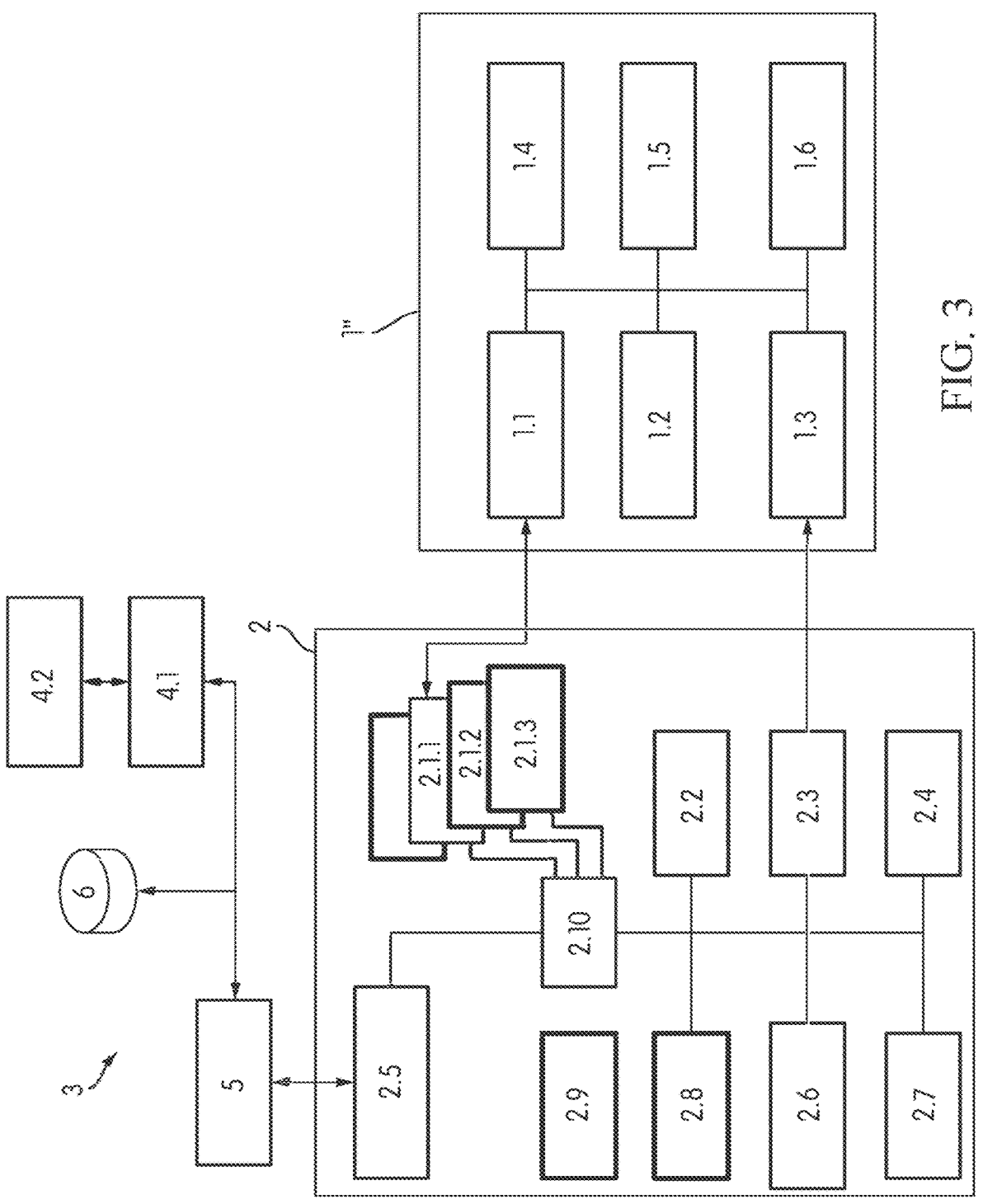
FIG. 3 is a schematic representation of an intraoral X-ray system with AEC functionality to which an IO X-ray sensor for operation in an AEC Plus mode is connected.

1.1 Communication interface
1.2 Exposure Analysis Unit
1.3 Imaging X-ray detector
1.4 Controller
1.5 Sensor-specific properties (memory)
1.6 Image memory
2. X-ray device
2.1.1 Communication interface
2.1.2 Communication interface
2.1.3 Communication interface
2.2 Decision unit
2.3 X-ray source
2.4 Controller
2.5 Communication interface
2.6 Power supply and high voltage source
2.7 User interface
2.8 Exposure analysis unit
2.9 Image memory
2.10 Functional (mode) switch
3. Intraoral X-ray system
4.1 Computer
4.2 User interface and display
5. Network
6. Cloud As shown in FIGS. 1 to 3 of different embodiments, the intraoral X-ray system (3) comprises an intraoral X-ray device (2) which is equipped with an automatic exposure control (AEC) functionality, and optionally connectable to a cloud (6) and a computer (4.1), wherein at least one intraoral X-ray sensor (1; 1'; 1") can be connected to the intraoral X-ray device (2), and the intraoral X-ray device (2) has a functional switch (2.10) which, in an initial identification process, recognizes the sensor type of the at least one connected intraoral Xray sensor (1; 1'; 1") and activates an associated mode (M; M'; M"). The intraoral X-ray system (3) comprises one or more of the following modes (M; M'; M"): a mode (M") for intraoral X-ray sensor side detection of an exposure level, a mode (M') for intraoral X-ray device, computer or cloud side detection of an exposure level, a mode (M) without detection of an exposure level.

AEC Plus Mode

In the following, the mode (M") corresponding to the AEC Plus mode explained at the beginning is described: FIG. 3 shows a schematic diagram of an intraoral X-ray system (3) according to an embodiment of the invention. The intraoral X-ray system (3) has an intraoral X-ray device (2) connected to an intraoral X-ray sensor (1") via communication interfaces (2.1.1; 1.1). The connection is preferably a cable connection. The IO X-ray sensor (1") consists of a sensor head (housing), cable and connector. The IO X-ray sensor (1") is connected to the intraoral X-ray device (2) via this connector. Additional X-ray sensors (1, 1',1") with or without AEC functionality, of different types, can preferably be connected simultaneously to the IO X-ray device (2) via their connectors. Alternatively, a wireless connection can be used. The intraoral X-ray sensor (1") has a communication interface (1.1), an exposure analysis unit (1.2), an imaging X-ray detector (1.3), a controller (1.4), a memory (1.5) containing sensor-specific properties, and an image memory (1.6). The image memory (1.6) stores part or all of the image data received from the imaging X-ray detector (1.3). The image memory (1.6) is useful if pixel image data from the imaging X-ray detector (1.3) cannot be read out for evaluation without loss of signal, or if loss of signal is unacceptable for reasons of radiation hygiene. Preferably, the X-ray sensor (1") can be equipped with a battery and wireless communication. This allows the cable to be dispensed with. A wired data communication and/or power supply can also be considered as an alternative. Here, a USB interface or Power over Ethernet (PoE) is provided as a standard.

The intraoral X-ray sensor (1") contains components for an automatic exposure control (AEC) functionality, which is explained in more detail below. The scout shot or scout video stream received from the imaging X-ray detector (1.3) is analyzed locally in the intraoral X-ray sensor (1") by the exposure analysis unit (1.2) to detect information on the exposure level. The analysis result including the exposure level information is forwarded to the intraoral X-ray device (2) or to another external device (e.g., a computer) by means of the communication interface (1.1). The intraoral X-ray device (2) has corresponding communication interfaces (2.1.1; 2.5) for this purpose. The intraoral X-ray unit (2) has a decision unit (2.2) which evaluates the analysis result including the detected information on the exposure level and decides on the sequence of further exposures, in particular the number of shots and their duration. In the case of a video stream, this can also be done during the ongoing exposure. When using a video stream, the first shot and second shot expands to the set of first "m" shots and second "n" shots. In this case, the process can also be repeated multiple times. The IO X-ray sensor (1") remains in corresponding recording readiness until the end of the recording session. The intraoral X-ray device (2) also has an X-ray source (2.3), a power supply and high-voltage source (2.6) and a controller (2.4). The decision unit (2.2) is further adapted to take into account sensor-specific properties and/or user-specified image quality parameters. The sensor-specific properties include information on sensor dimensions, local pixel errors, dose/signal behavior and the maximum saturation level above which saturation effects occur that allow no or limited digitization of the analog exposure signal. The image quality parameters can be entered by the user directly or indirectly through a user interface (2.7) on the X-ray device (2). An indirect specification can be made via the medical indication (e.g. clarification of suspected caries, paradentosis, root course), which is converted into exposure parameters by the intraoral X-ray system (3) with the decision unit (2.2), e.g. maximum exposure, dual energy, etc. Alternatively, this can also be specified via a user interface (4.2) of a computer (4.1) connected to the intraoral X-ray device (2). The intraoral X-ray device (2) is connected to the computer (4.1) via its communication interface (2.5) and preferably via a network (5). The intraoral X-ray device (2) and the computer (4.1) may also have a connection to a cloud (6). The received raw image material is processed into an initial raw image to compensate for sensor- and recording-specific deficiencies. These are: Gain, Blemish and DC correction (classic), dynamic range extension (or high dynamic range HDR), motion artifact compensation (anti-shake). Instead of the IO X-ray sensor or X-ray device (2) performing these and other image processing functions using respective, internal image memories (2.9;1.6), this can be performed in the cloud (6) or by the PC (4.1).

In this embodiment, the intraoral X-ray device (2) does have an exposure analysis unit (2.8), but this is not required because the IO X-ray sensor (1") performs the evaluation itself. Furthermore, the other thick outlined components are also not absolutely needed. Preferably, the communication interfaces (2.1.1) to (2.1.3) are provided separately or alternatively as a common communication interface.

AEC Mode

In the following, the mode (M') is described, which corresponds to the AEC mode explained at the beginning:

FIG. 2 shows a schematic diagram of an intraoral X-ray system (3) according to a further embodiment of the invention. The intraoral X-ray system (3) has an intraoral X-ray device (2) connected to an intraoral X-ray sensor (1') via communication interfaces (2.1.2;1.1). The connection is preferably a cable connection. The IO X-ray sensor (1') consists of a sensor head (housing), cable and connector. The IO X-ray sensor (1') is connected to the intraoral X-ray device (2) via this connector. Other sensors (1, 1',1") with or without AEC functionality can preferably be connected simultaneously to the IO X-ray device (2) via their connectors. Alternatively, a wireless connection can be used. The intraoral X-ray sensor (1') has a communication interface (1.1), no exposure analysis unit (1.2), an imaging X-ray detector (1.3), a controller (1.4), and a memory (1.5) containing the sensor specific properties. Preferably, the X-ray sensor (1') can be equipped with a battery and wireless communication. This allows to dispense with a cable. A wired data communication and/or power supply can also be considered alternatively. Here, a USB interface or Power over Ethernet (PoE) is provided as a standard.

The intraoral X-ray sensor (1') does not include components for automatic exposure control (AEC) functionality. The scout shot or scout video stream received from the imaging X-ray detector (1.3) is analyzed locally in the X-ray device (2) by the exposure analysis unit (2.8) to detect information on the exposure level. The intraoral X-ray device (2) has a decision unit (2.2) which evaluates the analysis result including the detected information on the exposure level and decides on the sequence of further exposures, in particular the number of shots and their duration. In the case of a video stream, this can also be conducted during the ongoing exposure. When using a video stream, the first shot and second shot expands to the set of first "m" shots and second "n" shots. In this case, the process can also be repeated multiple times. The IO X-ray sensor (1') remains in corresponding recording reediness until the end of the recording session. The intraoral X-ray device (2) also has an X-ray source (2.3), a power supply and high-voltage source (2.6) and a controller (2.4). The decision unit (2.2) is further adapted to take into account the sensor-specific properties and/or image quality parameters specified by the user. The sensor-specific properties include inter alia information on sensor dimensions, local pixel errors, dose/signal behavior and the maximum saturation level above which saturation effects occur that allow no or limited digitization of the analog exposure signal. The image quality parameters can be entered by the user directly or indirectly through a user interface (2.7) on the X-ray device (2). An indirect specification can be made via the medical indication (e.g. clarification of suspected caries, paradentosis, root course), which is converted into exposure parameters by the intraoral X-ray system (3) with the decision unit (2.2), e.g. maximum exposure, dual energy, etc. Alternatively, this can also be performed via a user interface (4.2) of a computer (4.1) connected to the intraoral X-ray device (2). The intraoral X-ray device (2) is connected to a computer (4.1) via its communication interface (2.5) and preferably via a network (5). The intraoral X-ray device (2) and the computer (4.1) may also have a connection to a cloud (6). The received raw image material is processed into an initial raw image to compensate for sensor- and recording-specific deficiencies. These are: Gain, Blemish and DC correction (classic), dynamic range extension (or high dynamic range (HDR)), motion artifact compensation (anti-shake). Instead of the X-ray sensor (1') or the X-ray device (2) performing image processing functions, this can be conducted in the cloud (6) or by the PC (4.1). The X-ray device (2) also has an image memory (2.9).

The communication interfaces (2.1.1) to (2.1.3) are preferably provided separately or alternatively as a common communication interface.

Standard Mode

In the following, the mode (M) is described, which corresponds to the standard mode explained at the beginning: FIG. 1 shows a schematic diagram of an intraoral X-ray system (3) according to a further embodiment of the invention. The intraoral X-ray system (3) has an intraoral X-ray device (2) connected to an intraoral X-ray sensor (1) via the communication interfaces (2.1.3; 1.1). The connection is preferably a cable connection. The IO X-ray sensor (1) consists of a sensor head (housing), cable and connector. The IO X-ray sensor (1) is connected to the intraoral X-ray device (2) via this connector. Preferably, further IO X-ray sensors (1, 1',1") with or without AEC functionality can be connected simultaneously to the IO X-ray device (2) via their connectors. Alternatively, a wireless connection can be used. The intraoral X-ray sensor (1) has a communication interface (1.1), no exposure analysis unit (1.2), an imaging X-ray detector (1.3), a controller (1.4), a memory (1.5) containing the sensor specific properties. Preferably, the IO X-ray sensor (1) can be equipped with a battery and wireless communication. This allows to dispense with a cable. A wired data communication and/or power supply can also be considered alternatively. Here, a USB interface or Power over Ethernet (PoE) is suitable as a standard.

The intraoral X-ray sensor (1) does not contain any components for automatic exposure control (AEC) functionality. The IO X-ray sensor (1) remains in corresponding recording readiness until the end of the recording session. The intraoral X-ray device (2) also has an X-ray source (2.3), a power supply and high-voltage source (2.6) and a controller (2.4).

The intraoral X-ray device (2) is connected to a computer (4.1) via its communication interface (2.5) and preferably via a network (5). The intraoral X-ray device (2) and the computer (4.1) can also have a connection to a cloud (6). Instead of the X-ray sensor (1) or the X-ray device (2) performing image processing functions, this can be performed in the PC (4.1). The X-ray device (2) may also have an image memory (2.9). The received raw image material is processed into an initial raw image to compensate for sensor and recording specific deficiencies. These are: Gain, Blemish and DC correction (classic), dynamic range extension (or high dynamic range (HDR)), motion artifact compensation (anti-shake).

In this embodiment, the intraoral X-ray device (2) has an exposure analysis unit (2.8), but this is not required in this constellation. Furthermore, the other components with thick borders are also not absolutely necessary.

The communication interfaces (2.1.1) to (2.1.3) can preferably be provided separately or alternatively as a common communication interface.

Three modes have been described in the present invention. Other modes with associated sensor types are also conceivable. Further communication interfaces can be added separately. Depending on their functionality, more or fewer functional components of the X-ray device (2) or X-ray system (3) become responsive. The functional mode switch (2.10) identifies the respective sensor type, activates the corresponding mode (M; M'; M") to also integrate the extended functional components.

The invention claimed is:

1. An intraoral X-ray system comprising:
an intraoral X-ray device which is equipped with an automatic exposure control (AEC) functionality and connectable to a cloud and a computer,
wherein at least one intraoral X-ray sensor is connectable to the intraoral X-ray device, and the intraoral X-ray device has a functional switch which, in an initial identification process, recognizes a built-in exposure analysis capability of the at least one connected intraoral X-ray sensor and activates an associated mode M, M', M" in response to the recognition, wherein the intraoral X-ray system further comprises one or more of the following modes: a mode M" for intraoral X-ray sensor side detection of an exposure level that is activated by the functional switch when the at least one intraoral X-ray sensor has built-in exposure analysis capability, a mode M' for intraoral X-ray device, computer or cloud side detection of an exposure level, or a mode M without detection of an exposure level that is activated by the functional switch when the at least one intraoral X-ray sensor does not have built-in exposure analysis capability.

2. The intraoral X-ray system according to claim 1, wherein the intraoral X-ray system includes an associated intraoral X-ray sensor including an exposure analysis circuitry, an imaging X-ray detector, and a communication interface, and wherein when operating in the mode M" for intraoral X-ray sensor side detection for an exposure level, a scout shot or a scout video stream received from the imaging X-ray detector is analyzed by the exposure analysis circuitry within the intraoral X-ray sensor to acquire information about the exposure level of the scout shot or the scout video stream and the information is forwarded by the communication interface to a decision circuitry of the intraoral X-ray device or another device that is arranged externally to the intraoral X-ray sensor, for evaluation and decision of further exposures.

3. The intraoral X-ray system according to claim 1, wherein the intraoral X-ray device includes an imaging X-ray detector, a communication interface, and an exposure analysis circuitry to provide the exposure analysis capability located in the intraoral X-ray device, wherein when operating in the mode M' for intraoral X-ray device, computer, or cloud side detection of an exposure level and an associated intraoral X-ray sensor does not detect information on exposure level, a scout shot or a scout video stream received from the imaging X-ray detector is forwarded to the intraoral X-ray device by the communication interface and is locally analyzed by the exposure analysis circuitry in the intraoral X-ray device to detect information about the exposure level of the scout shot or the scout video stream and the information is forwarded to a decision circuitry of the intraoral X-ray device, computer and/or cloud for evaluation and decision of further exposures.

4. The intraoral X-ray system according to claim 1, wherein when operating in the mode M without detection of an exposure level and an associated intraoral X-ray sensor that does not detect information on the exposure level, the intraoral X-ray device also does not detect information on the exposure level.

* * * * *